United States Patent
Robinson et al.

(10) Patent No.: US 10,556,044 B2
(45) Date of Patent: Feb. 11, 2020

(54) REDUCED-PRESSURE DRESSING CONNECTION PADS, SYSTEMS, AND METHODS

(71) Applicant: KCI Licensing, Inc., San Antonio, TX (US)

(72) Inventors: Timothy Mark Robinson, Shillingstone (GB); Christopher Brian Locke, Bournemouth (GB); Richard Daniel John Coulthard, Verwood (GB)

(73) Assignee: KCI Licensing, Inc., San Antonio, TX (US)

( * ) Notice: Subject to any disclaimer, the term of this patent is extended or adjusted under 35 U.S.C. 154(b) by 708 days.

(21) Appl. No.: 15/205,784

(22) Filed: Jul. 8, 2016

(65) Prior Publication Data

US 2016/0361473 A1 Dec. 15, 2016

Related U.S. Application Data

(60) Division of application No. 13/852,718, filed on Mar. 28, 2013, now Pat. No. 9,427,502, which is a (Continued)

(51) Int. Cl.
*A61M 1/00* (2006.01)
*A61F 13/00* (2006.01)
(Continued)

(52) U.S. Cl.
CPC ..... *A61M 1/0031* (2013.01); *A61F 13/00068* (2013.01); *A61F 13/0216* (2013.01);
(Continued)

(58) Field of Classification Search
CPC .............. A61M 1/0031; A61M 1/0092; A61M 1/0023; A61M 1/0088; A61M 1/0037;
(Continued)

(56) References Cited

U.S. PATENT DOCUMENTS 1,355,846 A 10/1920 Rannells
2,547,758 A 4/1951 Kelling
(Continued)

FOREIGN PATENT DOCUMENTS

AU 550575 B2 3/1986
AU 745271 B2 3/2002
(Continued)

OTHER PUBLICATIONS

International Search Report corresponding to PCT/US2011/027989, dated Nov. 24, 2011.
(Continued)

*Primary Examiner* — Andrew J Mensh (57) ABSTRACT

Systems, methods, and connectors are provided that introduce a working gas at certain times into a reduced-pressure dressing into order to break or avoid vacuum locks in the conduits removing fluids. In one instance, a reduced-pressure connector includes a connector body for applying a reduced pressure to the tissue site. The connector body is formed with a venting port, a body conduit, and a receptacle to receive a reduced-pressure delivery conduit. The reduced-pressure connector includes a flexible member coupled to the connector body over the venting port. The flexible member is formed with at least one venting aperture. The flexible member is biased away from the venting port and is configured to collapse and seal the venting port under a reduced pressure greater than a threshold pressure. Other systems, apparatuses, and methods are disclosed.

9 Claims, 5 Drawing Sheets

Related U.S. Application Data continuation of application No. 13/044,338, filed on Mar. 9, 2011, now Pat. No. 8,430,867.

(60) Provisional application No. 61/313,351, filed on Mar. 12, 2010.

(51) Int. Cl.
  *A61F 13/02* (2006.01)
  *A61M 39/24* (2006.01)

(52) U.S. Cl.
  CPC ........ *A61M 1/0023* (2013.01); *A61M 1/0088* (2013.01); *A61M 1/0092* (2014.02); *A61F 2013/0028* (2013.01); *A61M 1/0037* (2013.01); *A61M 2039/248* (2013.01); *A61M 2205/3344* (2013.01); *Y10T 29/49863* (2015.01)

(58) Field of Classification Search
  CPC ..... A61M 2039/248; A61M 2205/3344; A61F 13/00068; A61F 13/0216; A61F 2013/0028; Y10T 29/49863
  USPC .......................................................... 604/317
  See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,557,778 A | 1/1971 | Hughes |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0222527 A1* | 10/2005 | Miller ................. A61M 1/0088 602/1 |
| 2007/0016152 A1* | 1/2007 | Karpowicz ........... A61M 1/001 604/326 |
| 2007/0179460 A1* | 8/2007 | Adahan ............... A61M 1/0066 604/319 |
| 2009/0043268 A1 | 2/2009 | Eddy et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |

(56) References Cited

FOREIGN PATENT DOCUMENTS

| | | |
|---|---|---|
| GB | 2 235 877 A | 3/1991 |
| GB | 2 329 127 A | 3/1999 |
| GB | 2 333 965 A | 8/1999 |
| GB | 2409412 A | 6/2005 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2007087810 A2 | 8/2007 |
| WO | 2008100440 A1 | 8/2008 |
| WO | 2009071933 A2 | 6/2009 |
| WO | 2009124100 A1 | 10/2009 |
| WO | 2009156984 A2 | 12/2009 |

OTHER PUBLICATIONS

European Search Report corresponding to EP15163545.5, dated Aug. 21, 2015.
Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp: 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

Chinese 1st Office Action corresponding to Chinese Application No. 201510187894.4, dated Aug. 24, 2016.

\* cited by examiner

REDUCED-PRESSURE DRESSING CONNECTION PADS, SYSTEMS, AND METHODS

RELATED APPLICATIONS

The present invention is a Divisional of U.S. patent application Ser. No. 13/852,718, entitled "Reduced-Pressure Dressing Connection Pads, Systems, and Methods," filed Mar. 28, 2013, which is a Continuation of U.S. patent application Ser. No. 13/044,338, now U.S. Pat. No. 8,430,867, entitled "Reduced-Pressure Dressing Connection Pads, Systems, and Methods," filed Mar. 9, 2011, which claims the benefit, under 35 USC § 119(e), of the filing of U.S. Provisional Patent Application Ser. No. 61/313,351, entitled "Reduced-Pressure Dressing Connection Pads, Systems, and Methods," filed Mar. 12, 2010, which is incorporated herein by reference for all purposes.

BACKGROUND

The present disclosure relates generally to tissue treatment systems and more particularly to reduced-pressure connection pads, systems, and methods.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced-pressure therapy," or "vacuum therapy") provides a number of benefits, which may include faster healing and increased formulation of granulation tissue. Typically, reduced pressure is applied to tissue through a porous pad or other manifolding device. The porous pad distributes reduced pressure to the tissue and channels fluids that are drawn from the tissue. The porous pad often is incorporated into a dressing having other components that facilitate treatment.

SUMMARY

According to an illustrative embodiment, According to an illustrative embodiment, a reduced-pressure connector for use with a reduced-pressure system for treating a tissue site includes a connector body for applying a reduced pressure to the tissue site through a sealing member. The connector body is formed with a body conduit for fluidly coupling to a reduced-pressure delivery conduit that supplies reduced pressure and a venting port. The reduced-pressure connector further includes a flexible member coupled to the connector body over the venting port. The flexible member is formed with at least one venting aperture. The flexible member is biased away from the venting port and is configured to collapse and seal the venting port under a reduced pressure greater than a threshold reduced pressure.

According to another illustrative embodiment, a system for treating a tissue site on a patient with reduced pressure includes a manifold for disposing adjacent to the tissue site, a sealing member, and a reduced-pressure connector. The sealing member has a first side and a second, tissue-facing side. The second-tissue facing side of the sealing member is for disposing adjacent the manifold and a portion of the patient's epidermis. The sealing member has a supply aperture and a port aperture. The reduced-pressure connector is for coupling to the sealing member to supply reduced pressure to the manifold. The reduced-pressure connector includes a connector body formed with a body conduit having a first end and a second end. The second end of the body conduit is fluidly coupled to the supply aperture. The reduced-pressure connector further includes a venting port formed in the connector body for providing fluid communication with the port aperture. The reduced-pressure connector also includes a flexible member coupled to the connector body over the venting port. The flexible member is formed with at least one venting aperture. The flexible member is biased away from the venting port and is configured to collapse to seal the venting port under a reduced pressure greater than a threshold pressure. The system further includes a reduced-pressure source in fluid communication with the reduced-pressure connector through a reduced-pressure delivery conduit. The flexible member returns to an extended position in response to the reduced pressure being less than the threshold pressure. When the flexible member is in the extended position, the reduced-pressure connector is configured such that a working gas from outside the flexible member is communicated through the at least one venting aperture, venting port, and port aperture to the tissue site for extraction by the body conduit for alleviating a vacuum lock.

According to another illustrative embodiment, a method for treating a tissue site on a patient with reduced pressure includes deploying a manifold adjacent the tissue site and deploying a sealing member over the manifold and a portion of the patient's epidermis to form a sealed space. The sealing member has a port aperture and a supply aperture. The method further includes coupling a reduced-pressure connector to the sealing member to provide reduced pressure to the sealed space. The reduced-pressure connector includes a connector body having a venting port that is fluidly coupled to the port aperture of the sealing member. The method also includes fluidly coupling a reduced-pressure source to the reduced-pressure connector. The reduced-pressure connector includes the connector body formed with a body conduit having a first end and a second end. The second end of the body conduit is fluidly coupled to the supply aperture. The reduced-pressure connector also includes a flexible member coupled to the connector body over the venting port. The flexible member is formed with at least one venting aperture. The flexible member is biased away from the venting port and is configured to collapse to seal the venting port under a reduced pressure greater than a threshold pressure.

According to another illustrative embodiment, a method of manufacturing a reduced-pressure connector for applying a reduced pressure to a tissue site on a patient through a sealing member includes forming a connector body and forming a body conduit in the connector body having a first end and a second end. The first end is for fluidly coupling to a reduced-pressure delivery conduit that supplies reduced pressure and the second end is for delivering reduced pressure to a manifold. The method also includes forming a venting port in the connector body, coupling a flexible member to the connector body over the venting port, and forming at least one venting aperture in the flexible member. The flexible member is biased away from the venting port and is configured to collapse and seal the venting port under a reduced pressure greater than a threshold reduced pressure.

According to another illustrative embodiment, a system for treating a tissue site on a patient with reduced pressure includes a manifold for disposing adjacent to the tissue site and a sealing member having a first side and a second, tissue-facing side. The second-tissue facing side is for disposing adjacent the manifold and a portion of the patient's epidermis. The sealing member has a supply aperture and a port aperture. The system also includes a reduced-pressure connector having a connector body formed with a venting port and a body conduit having a first end and a second end. The reduced-pressure connector also includes a dressing valve coupled to the connector body over the venting port. The dressing valve includes a valve body having a chamber, at least one venting aperture, and a venting port. The dressing valve further includes a ball disposed within the chamber and a spring biasing the ball towards a seat. When the ball is against the seat an opening of the venting port into the chamber is sealed and the at least one venting aperture is sealed. The spring is configured such that the ball overcomes the biasing of the spring when exposed to a reduced pressure greater than a relief pressure whereupon a working gas enters the at least one venting aperture and is communicated to the venting port.

According to another illustrative embodiment, a method for preventing a vacuum lock during a reduced-pressure treatment of a tissue site on a patient includes applying a reduced pressure to the tissue site utilizing a treatment system to reach a reduced pressure, sealing a dressing valve of the treatment system at a first threshold pressure, and unsealing the dressing valve to release a working gas into one or more venting apertures of the dressing valve for extraction by a body conduit of the treatment system to alleviate vacuum lock.

According to another illustrative embodiment, a method for preventing a vacuum lock during a reduced-pressure treatment of a tissue site on a patient includes applying a reduced pressure to the tissue site at a reduced pressure utilizing a treatment system, increasing the reduced pressure applied to the wound by the treatment system, determining the reduced pressure applied to the tissue site by the treatment system, venting a working gas through a dressing valve of the treatment system to a reduced-pressure delivery conduit in fluid communication with a reduced-pressure source to alleviate any vacuum locks in response to determining that the reduced pressure has reached a relief pressure, and resealing the dressing valve.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
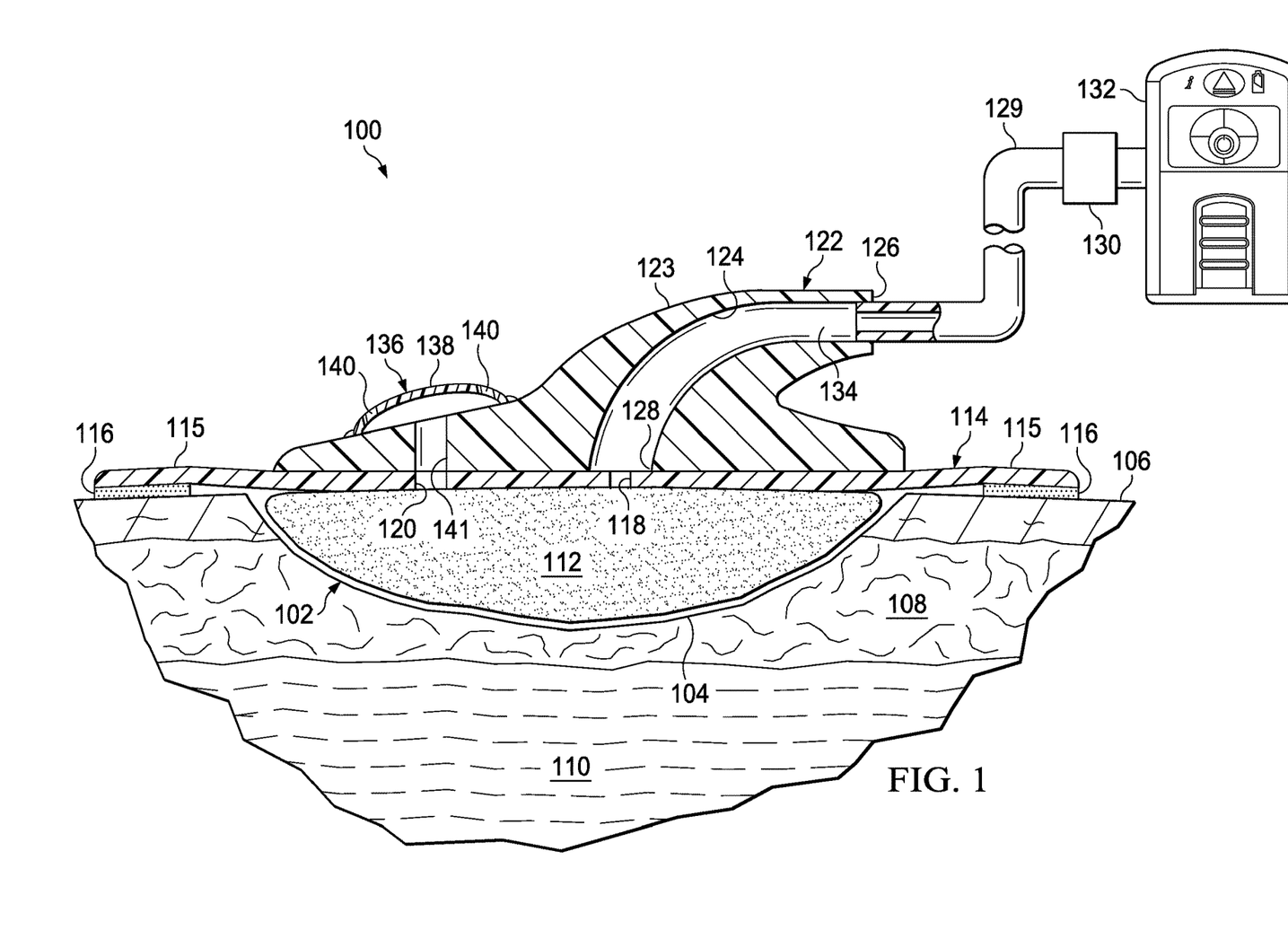
FIG. 1 is a schematic diagram with a portion shown in cross section of a reduced-pressure treatment system in accordance with an illustrative embodiment.
Figure 2:
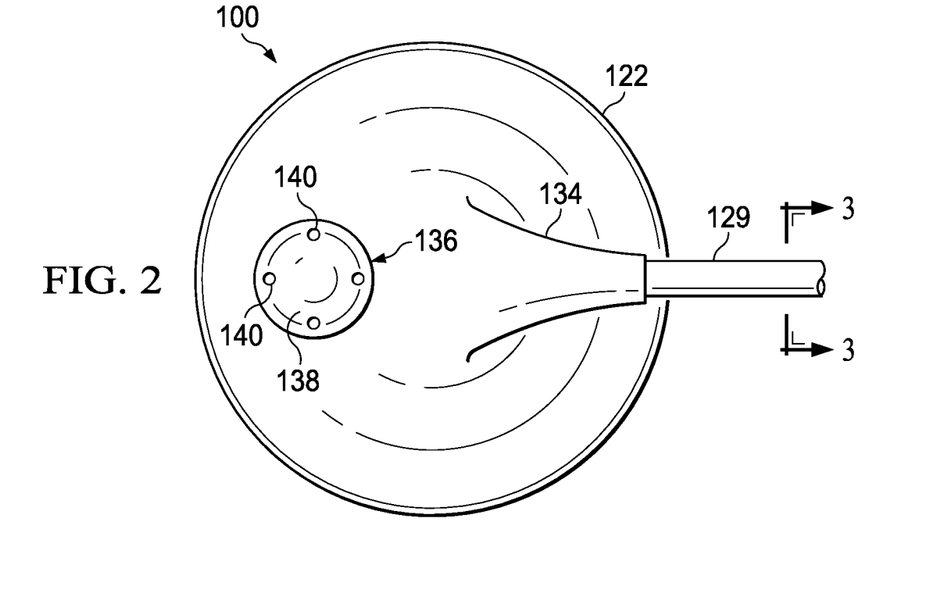
FIG. 2 is a top view of the reduced-pressure connector of FIG. 1 in accordance with an illustrative embodiment.

Referring primarily to FIGS. 1-5 and initially to FIG. 1, a reduced-pressure treatment system 100 is shown. The reduced-pressure treatment system 100 is utilized to treat a tissue site 102. The tissue site 102 may be the bodily tissue of any human, animal, or other organism including bone tissue, adipose tissue, muscle tissue, dermal tissue, vascular tissue, connective tissue, cartilage, tendons, ligaments, or any other tissue. Unless otherwise indicated, "or" as used herein does not require mutual exclusivity. The tissue site 102 may be a wound 104. The wound 104 may take numerous possible shapes and degrees, and in this illustrative example is shown as a wound extending through epidermis 106, dermis 108, and into subcutaneous tissue 110.

The reduced-pressure treatment system 100 may include a manifold 112, a sealing member 114, and a reduced-pressure connector 122. The reduced-pressure connector 122 includes a connector body 123. The connector body 123 may have a body conduit 124 with a first end 126 and a second end 128. The first end 126 may be or include a receptacle 134. The receptacle 134 is for receiving a reduced-pressure delivery conduit 129. The reduced-pressure connector 122 also includes a dressing valve 136.

The term "manifold" as used herein generally refers to a substance or structure that is provided to assist in applying reduced pressure to, delivering fluids to, or removing fluids from a tissue site 102. The manifold 112 typically includes a plurality of flow channels or pathways that distribute fluids provided to and removed from the tissue site 102 around the manifold 112. In one illustrative embodiment, the flow channels or pathways are interconnected to improve distribution of fluids provided or removed from the tissue site 102. The manifold 112 may be a biocompatible material that is capable of being placed in contact with the tissue site 102 and distributing reduced pressure to the tissue site 102. Examples of manifolds 112 may include, without limitation, devices that have structural elements arranged to form flow channels, such as, for example, cellular foam, open-cell foam, porous tissue collections, liquids, gels, and foams that include, or cure to include, flow channels. The manifold 112 may be porous and may be made from foam, gauze, felted mat, or any other material suited to a particular biological application. In one embodiment, the manifold 112 is a porous foam and includes a plurality of interconnected cells or pores that act as flow channels. The porous foam may be a polyurethane, open-cell, reticulated foam such as Granu-Foam® material manufactured by Kinetic Concepts, Incorporated of San Antonio, Tex. Other embodiments may include "closed cells." In some situations, the manifold 112 may also be used to distribute fluids such as medications, antibacterials, growth factors, and various solutions to the tissue site 102. Other layers may be included in or on the manifold 112, such as absorptive materials, wicking materials, hydrophobic materials, and hydrophilic materials.

In one illustrative, non-limiting embodiment, the manifold 112 may be constructed from bioresorbable materials that may remain in a patient's body following use of the reduced-pressure treatment system 100. Suitable bioresorbable materials may include, without limitation, a polymeric blend of polylactic acid (PLA) and polyglycolic acid (PGA). The polymeric blend may also include without limitation polycarbonates, polyfumarates, and capralactones. The manifold 112 may further serve as a scaffold for new cell-growth, or a scaffold material may be used in conjunction with the manifold 112 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Any material or combination of materials may be used for the manifold material provided that the manifold 112 is operable to distribute the reduced pressure and allows the flow of fluids or liquids. In some illustrative embodiments, the manifold 112 may also be a combination or layering of materials. For example, a first manifold layer of hydrophilic foam may be disposed adjacent to a second manifold layer of hydrophobic foam to form the manifold 112.

Fluids may flow from the tissue site 102 through the manifold 112, through a supply aperture 118 in the sealing member 114 into the body conduit 124. The fluids flow from the body conduit 124 out of the receptacle 134 into the reduced-pressure delivery conduit 129 and into a reduced-pressure source 132. The reduced-pressure source 132 may include a chamber or reservoir for receiving the fluids.

The reduced-pressure treatment system 100 includes the sealing member 114. The sealing member 114 may include a supply aperture 118 and a port aperture 120. The sealing member 114 is fluidly coupled to the reduced-pressure connector 122. The sealing member 114 covers the manifold 112 and typically extends past a peripheral edge of the manifold 112 to form a drape extension 115. The drape extension 115 may be sealed against the patient's epidermis 106 by an attachment device 116.

An attachment device 116 may be used to hold the sealing member 114 against the patient's epidermis 106 or another layer, such as a gasket or additional sealing member. The attachment device 116 may take numerous forms. For example, the attachment device 116 may be a medically acceptable, pressure-sensitive adhesive that extends about a periphery, a portion, or the entire sealing member 114. As additional examples, the attachment device 116 may be a sealing tape, drape tape or strip, double-sided drape tape, paste, hydrocolloid, hydro gel or other sealing devices or elements.

If a tape is used the tape may be formed of the same material as the sealing member 114 with a pre-applied pressure sensitive adhesive. The adhesive may be applied on a tissue-facing, or patient-facing side, of the sealing member 114. The sealing member 114 and corresponding attachment device 116 provide a fluid seal between the sealing member 114 and the epidermis 106 of the patient. "Fluid seal," or "seal," means a seal adequate to maintain reduced pressure at a desired site given the particular reduced-pressure source 132 or subsystem involved. Before the sealing member 114 is secured to the patient, the attachment device 116 may have removable strips covering the attachment device 116, which are removed for treatment of the patient.

The sealing member 114 may be any material that provides a fluid seal. The sealing member 114 may be, for example, an impermeable or semi-permeable, elastomeric material. "Elastomeric" means having the properties of an elastomer. Elastomeric material generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of sealing member materials include a silicone drape, a 3M Tegaderm® drape, or a polyurethane (PU) drape such as one available from Avery Dennison Corporation of Pasadena, Calif.

All or portions of the reduced-pressure connector 122 may also be formed from a polymer. The reduced-pressure connector 122 may be molded, cast, or otherwise generated from a single material and molds or multiple materials and distinct molds. Additional materials utilized alone or in combination to form all or portions of the reduced pressure connector 122 may include polyurethane, thermoplastic polyurethane, thermoplastic elastomers, silicone, polyvinyl chloride, or other suitable materials.

The reduced-pressure source 132 provides reduced pressure. The reduced-pressure source 132 may be any device for supplying a reduced pressure, such as a vacuum pump, wall suction, micro-pump, or other source. While the amount and nature of reduced pressure applied to a tissue site will typically vary according to the application, the reduced pressure will typically be between −5 mm Hg and −500 mm Hg and more typically between −75 mm Hg and −300 mm Hg. For example, and not by way of limitation, the pressure may be −80, −90, −100, −110, −120, −130, −140, −150, −160, −170, −180, −190, −200, −210 mm Hg or another pressure.

The reduced-pressure source 132 may include a display, information indicator, battery light, reservoir, full or blocked indicator, power switch, speaker, alarm system, keypad or any number of other interfaces for receiving user input. In particular, the reduced-pressure source 132 may be programmed or set to turn on at one pressure or threshold and to turn off at another pressure or secondary threshold. The thresholds may be set utilizing an electronic user interface or utilizing mechanical regulation elements. The reduced-pressure source 132 may provide reduced pressure for a time period that is programmed by a user or pre-programmed.

In one embodiment the reduced-pressure source 132 may include one or more pressure sensors that may be utilized to detect a pressure applied to the tissue site 102. For example, pressures communicated by one or more lumens in the reduced-pressure delivery conduit 129 may be sensed by the pressure sensors in the reduced-pressure source 132 for governing the reduced pressure applied. The reduced pressure supplied by the reduced-pressure source 132 is delivered through the reduced-pressure delivery conduit 129 to the reduced-pressure connector 122.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Reduced pressure may initially generate fluid flow in the manifold 112, reduced-pressure delivery conduit 129, and proximate the tissue site 102. As the hydrostatic pressure around the tissue site 102 approaches the desired reduced pressure, the flow may subside, and the reduced pressure may be maintained. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, unless otherwise indicated, an increase in reduced pressure or vacuum pressure typically refers to a relative reduction in absolute pressure.

One or more devices 130 may be added to the reduced-pressure delivery conduit. For example, the device 130 may be a fluid reservoir, or collection member, to hold exudates and other fluids removed. Other examples of devices 130 that may be included on the reduced-pressure delivery conduit or otherwise fluidly coupled to the reduced-pressure delivery conduit include the following non-limiting examples: a pressure-feedback device, a volume detection system, a blood detection system, an infection detection system, a flow monitoring system, a temperature monitoring system, or other device. Some of these devices may be formed integrally with the reduced-pressure source 132.

In some cases, an extended fluid column in the body conduit 124, reduced-pressure delivery conduit 129, or elsewhere may inhibit or prevent the removal of fluids. The situation may induce a vapor lock (including a partial vapor lock). The vapor lock makes fluid removal difficult. The vapor lock may also cause the reduced pressure applied at the tissue site 102 to drop or be inhibited. The reduced-pressure connector 122 described herein and the associated dressing valve 136 may alleviate vapor lock by breaking up or preventing columns of fluid.

The dressing valve 136 includes a flexible member 138, one or more venting apertures 140, and a venting port 141. The dressing valve 136 may be utilized to provide a working gas, e.g., air or nitrogen, to the tissue site 102. The dressing valve 136 may also communicate with a clean or dedicated source of working gas. For example, the working gas may be a pressurized working gas, such as a medical grade nitrogen supplied through a canister fluidly communicating with the dressing valve 136 through the one or more venting apertures 140.

The reduced-pressure connector 122 facilitates delivery of reduced pressure through the sealing member 114 to a sealed space that is formed under the sealing member 114. The reduced pressure is delivered through the supply aperture 118 of the sealing member 114. The reduced pressure is further communicated to the venting port 141 of the dressing valve 136 through the port aperture 120 of the sealing member 114. The port aperture 120 and the venting port 141 may be aligned during deployment of the reduced-pressure connector 122 on the sealing member 114. The body conduit 124 may be similarly aligned with the supply aperture 118 of the sealing member 114. In an alternative embodiment, an ancillary supply conduit (not explicitly shown) may directly deliver reduced pressure from the body conduit 124 to the dressing valve 136. The ancillary supply conduit may be conduit formed in the connector body 123 that fluidly couples the body conduit 124 and the interior of the dressing valve 136. The opening of the ancillary supply conduit into the interior of the dressing valve 136 in this embodiment is the venting port 141.

In some circumstances, the body conduit 124 or the reduced-pressure delivery conduit 129 may become blocked or experience a vacuum lock. For example, a large amount of fluid may create a vacuum lock within the body conduit 124 preventing the removal of the fluids as well as application of the reduced pressure to the tissue site 102. The dressing valve 136 may function to alleviate (reduce or eliminate) the vacuum lock associated with the reduced-pressure delivery conduit 129 and the reduced-pressure source 132. The vacuum lock may also be referred to as a fluid lock, vapor lock, air lock, or liquid lock.

The dressing valve 136 includes the venting port 141, a flexible member 138, and the one or more venting apertures 140. The port aperture 120 and venting port 141 provide fluid communication between an interior of the dressing valve 136 and the manifold 112. The flexible member 138 is a flexible cover that is biased away from the port aperture 120. The collective area of the one or more venting apertures 140 is typically less than the area of the venting port 141. Upon being subjected to at least threshold reduced pressure that is delivered to the interior of the dressing valve 136, the flexible member 138 collapses and seals the port aperture 120. The flexible member 138 may be integrated with the connector body 123. For example, the connector body 123 and flexible member 138 may be formed or molded as an integral member. Alternatively, the flexible member 138 may be attached or coupled to the connector body 123 utilizing adhesives, tape, a base unit and locking mechanism, weld (RF or thermal), bond, cement, or device or technique. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Fluid coupling means that fluid may be in communication between the designated parts or locations.

Figure 5:
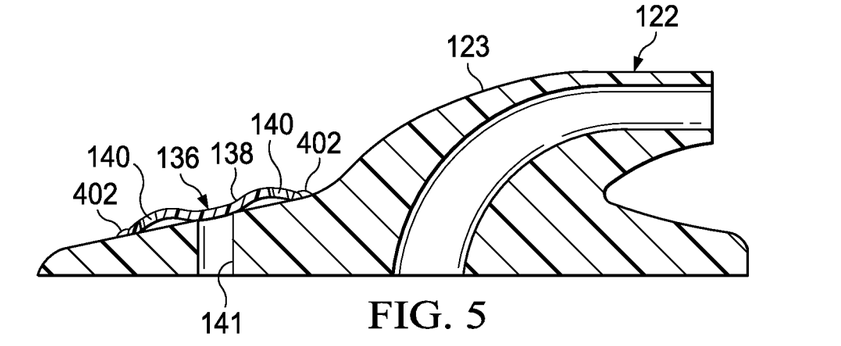
FIG. 5 is a cross sectional view of the reduced-pressure connector of FIGS. 1 and 4 shown with the dressing valve in a collapsed position in accordance with an illustrative embodiment.

The flexible member 138 is biased away from the venting port 141, but collapses to a retracted position (collapsed position) and seals the venting port 141 as shown in FIG. 5. The flexible member 138 may be biased utilizing materials, springs, dampeners, or other passive or active biasing elements to ensure that the port aperture 120 is not sealed unless the threshold reduced pressure is experienced. Collapse as herein used may include bending, deforming or otherwise moving to completely or partially seal the port aperture 120. The reduced pressure at which the flexible member 138 seals off the venting port 141 may vary based on the thickness, cross-sectional shape of the flexible member 138, the corresponding material, the difference in area between the venting apertures 140 and the venting port 141, or other factors.

The flexible member 138 is formed to include the one or more venting apertures 140. The venting apertures 140 may allow a working gas to pass through the flexible member 138 into the interior of the dressing valve 136. A working gas that passes through the venting apertures 140 may be communicated through the venting port 141 and port aperture 120 to the manifold 112 for extraction through the body conduit 124.

The venting apertures 140 may include filters, membranes or other similar elements (not shown) that may inhibit the entry of bacteria, viruses or other airborne particles into the dressing valve 136. The flexible member 138 may also include a cover that may be turned, lifted or otherwise engaged to turn on, off, or regulate the working gas flow through the venting apertures 140. For example, the cover may be turned or moved to partially block the working gas flow through the venting apertures 140.

Figure 3:
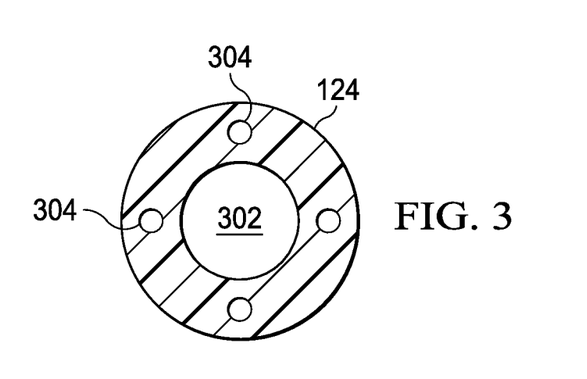
FIG. 3 is a cross sectional view of the reduced-pressure delivery conduit of FIG. 2 taken along line 3-3.

Referring primarily now to FIG. 3, the reduced-pressure delivery conduit 129 may include a primary lumen 302 and secondary lumens 304. In one embodiment, the primary lumen 302 may be utilized to extract fluids, such as exudates, from the tissue site 102 and apply the reduced pressure provided from the reduced-pressure source 132. The secondary lumens 304 represent one or more outer or ancillary lumens within the reduced-pressure delivery conduit. For example, one or more of the secondary lumens 304 may measure the reduced pressure at the tissue site 102 by allowing the reduced-pressure source 132 and corresponding pressure sensors therein to measure the reduced pressure applied at the tissue site 102 (or at the manifold 112, which should be at approximately the same pressure as the tissue site 102). In particular the primary lumen 302 and the secondary lumens 304 represent individual or isolated conduits that extend from the reduced-pressure source 132 to the reduced-pressure connector 122 in order to apply and measure the reduced pressure as described herein.

In another embodiment, the reduced-pressure delivery conduit 129 may include one or more wires, electrical cords for powering, controlling or communicating electric signals between the reduced-pressure source 132 and the reduced-pressure connector 122 or dressing valve 136. In an alternative embodiment, the dressing valve 136 may be electronically actuated or controlled utilizing control signals sent from the reduced-pressure source 132. For example, the reduced-pressure source 132 may control the opening or closing of the dressing valve 136 based on determined pressure thresholds and using a solenoid. As a result, the dressing valve 136 may be opened, activated, or engaged to vent air to remove a vacuum lock based on conditions, circumstances, or factors that may indicate a vacuum lock has or is occurring within the reduced-pressure system. In one embodiment, one of the secondary lumens 304 may include the wire connected to a sensor or the dressing valve 136. The secondary lumens 304 may allow the wire to be extended therein for an electronic sensor or dressing valve 136.

Figure 4:
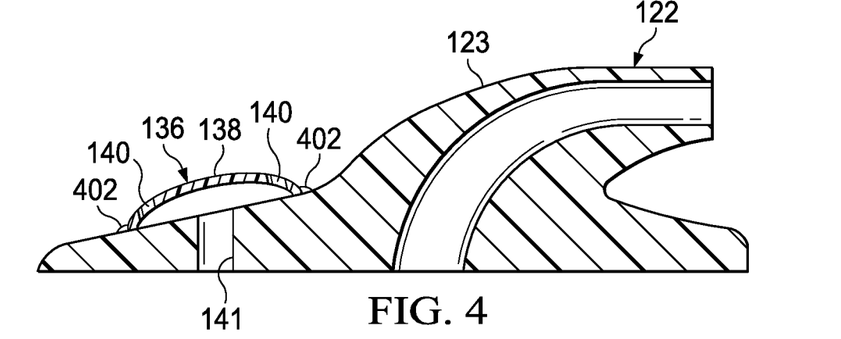
FIG. 4 is a cross sectional view of the reduced-pressure connector of FIG. 1 shown with a dressing valve in an extended position in accordance with an illustrative embodiment.

Referring now primarily to FIG. 4, the reduced-pressure connector 122 is shown with the flexible member 138 in a default, biased, or extended position or state. The flexible member 138 may be biased to urge the flexible member 138 away from the venting port 141 when the reduced pressure on the interior of the flexible member 138 is below a specified value or threshold pressure. The pressure on the interior surface applied to the flexible member 138 is approximately the pressure experienced by the tissue site 102.

Bonds 402 may be used connect the flexible member 138 to the connector body 123. For example, the bonds 402 may be glue, plastic weld, ultrasonic or RF welds, cements, adhesives, mechanical fasteners (such as clips, snaps, or other similar elements that connect the flexible member 138 to the connector body 123 and create a substantially airtight connection). As shown, the flexible member 138 includes one or more venting apertures 140 which may include multiple points allowing air from the surrounding environment or another working gas to enter into the dressing valve 136. The one or more venting apertures 140 may be sized and shaped to allow a specified amount of airflow through the flexible member 138 based on the venting needs of the reduced-pressure connector 122.

Referring now primarily to FIG. 5, the reduced-pressure connector 122 is shown with the flexible member 138 collapsed to seal the venting port 141. When collapsed (retracted), the flexible member 138 allows the reduced pressure at the manifold 112 to increase.

In another embodiment, the reduced-pressure connector 122 may include a lip (not shown) formed as an aspect of the connector body 123. The lip may be formed to align with the periphery of the venting port 141 in order to facilitate the flexible member 138 sealing the port aperture 120 when in the collapsed (retracted) position.

Referring now primarily to FIGS. 1-5, in operation according to one illustrative embodiment, the reduced-pressure treatment system 100 is applied to treat the tissue site 102, e.g., the wound 104, by placing the manifold 112 adjacent the wound 104, providing a fluid seal over the manifold 112 and a portion of the epidermis 106 by using the sealing member 114, attaching the reduced-pressure connector 122, and activating the reduced-pressure source 132.

The reduced-pressure connector 122 delivers reduced pressure to the manifold 112, which distributes the reduced pressure to the tissue site 102. The reduced-pressure treatment system 100 will typically continue to apply reduced pressure until a reservoir or canister of the reduced-pressure source 132 or external reservoir becomes full. The status of a reservoir or canister may be visually or electronically monitored with alerts generated to inform a user of a blockage or the canister or reservoir being filled.

The reduced-pressure source 132 applies reduced pressure to the tissue site 102 and the dressing valve 136. Reduced pressure is experienced on the interior or a portion of the flexible member 138 of the dressing valve 136. At a threshold reduced pressure, the flexible member 138 collapses under the influence of reduced pressure as shown in FIG. 5 to seal the venting port 141 thereby allowing the reduced pressure to increase at the manifold 112 and to remain unvented. The reduced-pressure source 132 may be configured to turn off or maintain a specified reduced pressure. For example, once the reduced-pressure source 132 has provided a reduced pressure at the tissue site 102 for a set time or upon reaching a desired pressure, the reduced-pressure source 132 may turn itself off. Once the reduced pressure decreases (increases on an absolute scale) to be lower than the threshold pressure, the flexible member 138 returns to the open state or extended position as shown in FIGS. 1 and 4, and the working gas enters the one or more vent apertures 140. The addition of the working gas helps to alleviate any vapor locks.

The dressing valve 136 as well as a control system of the reduced-pressure source 132 may be utilized to control the reduced pressure waveform applied to the tissue site 102. The waveform indicates the time and reduced pressure provided by the reduced-pressure source 132 and communicated to the reduced-pressure connector 122. The dressing valve 136 may include any number of venting apertures 140. For example, one or more venting apertures 140 may be formed within the flexible member 138. In another embodiment, the dressing valve 136 may not include venting apertures 140, such as when the flexible member 138 may be formed of a material that is semi-permeable to gases. As a result, the semi-permeable material may allow air to seep through the flexible member 138 at a known rate thereby fulfilling the functions of the venting apertures 140 as described herein.

Figure 6:
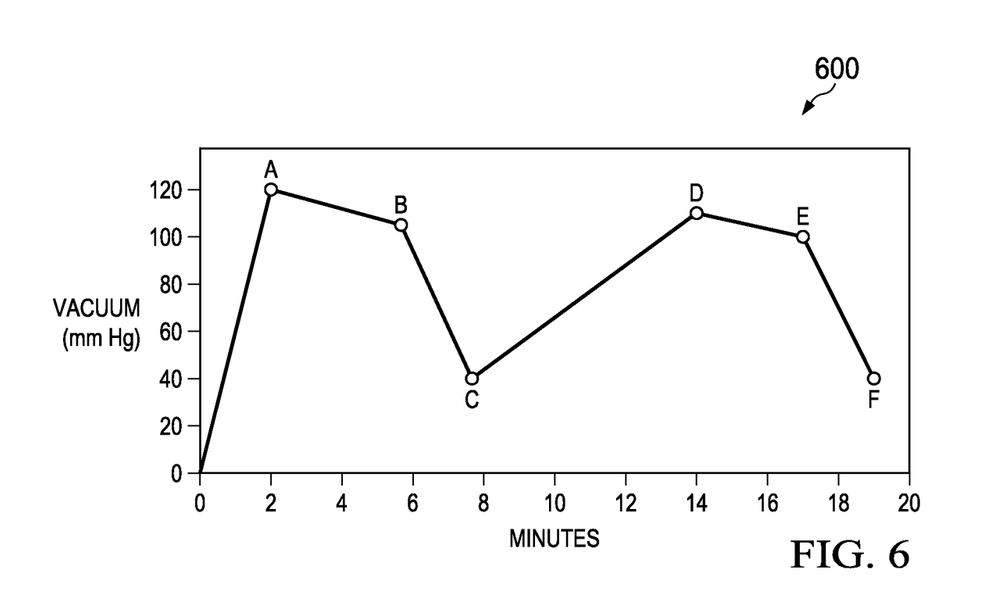
FIG. 6 is a graph illustrating pressure applied by the reduced-pressure connector over time in accordance with an illustrative embodiment (values on ordinate are negative)

Referring now primarily to FIG. 6, a chart or graph illustrating pressure applied by the reduced-pressure connector 122 over time is presented. In one embodiment, the reduced pressure may be measured in mm Hg on the y (ordinate) axis and time in minutes on the x (abscissa) axis. It should be noted that ordinate indicates negative gauge pressure. The pressures and corresponding time periods of FIG. 6 are shown for illustrative purposes only. The reduced pressures applied through the reduced-pressure treatment system 100 may vary as well as the time over which the reduced pressures are incremented, decremented, or maintained.

Referring primarily to FIGS. 1 and 6, a chart 600 includes various points that may correspond to utilization of the reduced-pressure treatment system 100. In particular points A, B, C, D, E and F of chart 600 may represent increases and decreases in reduced pressure applied to the tissue site 102 based on positions of the dressing valve 136. The example illustrated by chart 600 shows the initial pressure beginning at zero. A user, such as a doctor, patient, nurse or other medical professional, may activate the reduced-pressure source 132 at which point the reduced-pressure source 132 may begin increasing the reduced pressure applied to the reduced-pressure connector 122 and according to the tissue site 102.

Somewhere before point A (i.e., −120 mm Hg in this embodiment), the threshold pressure is reached and the flexible member 138 of the dressing valve 136 collapses to seal the venting port 141 thereby preventing air from venting through the dressing valve 136 to the tissue site 102. The threshold pressure may be, for example, −90, −95, −100, −105, −110, or −115 mm Hg or another pressure. At point A, the reduced-pressure source 132 determines that the reduced-pressure treatment system 100 is at the desired pressure (e.g., −125 mm Hg) or a higher or maximum threshold. The desired pressure may be specified, selected, programmed or otherwise configured for implementation by the reduced-pressure source 132. Between point A and B the dressing valve 136 has been sealed and the supply of reduced pressure has been terminated. The flexible member 138 may remain collapsed thereby blocking the venting port 141 from receiving air from the environment. Between point A and B, the reduced pressure is applied to the tissue site 102 and corresponding wound 104 allowing the fluids to be drained and providing the benefits of reduced pressure as currently known. The reduced pressure applied to the tissue site 102 between points A and B may naturally decrease as fluids are removed, based on natural leakage, or based on venting introduced into the reduced-pressure treatment system 100.

At point B the threshold pressure is reached and the dressing valve 136 opens. For example, the bias inherent in the flexible member 138 may overcome the reduced pressure exerted on the flexible member 138 through the venting port 141 causing the dressing valve 136 to reopen. At that point, the venting port 141 is opened and air or another working gas is vented through the venting apertures 140 of the flexible member 138 through the port aperture 120 of the sealing member 114 for extraction by the reduced-pressure delivery conduit. In one embodiment, the dressing valve 136 may be sealed and opened at approximately the same reduced pressure, such as −110 mm Hg, −120 mm Hg, −130 mm Hg, or another pressure.

As a result, the reduced pressure decreases significantly between point B and point C as opposed to the natural or minimal leakage that occurs between points A and B. At point C, the reduced-pressure source 132 determines that the reduced pressure has reached a minimum value and begins delivering reduced pressure again. Alternatively or in addition, the reduced-pressure source 132 may be activated by a timer. Once the lower or minimum pressure is reached or time duration reached, the reduced-pressure source 132 once again begins to apply reduced pressure to the tissue site 102 through the reduced-pressure connector 122. Points D, E and F correspond to the actions previously described for points A, B, and C, respectively. In another embodiment, the dressing valve 136 may be configured to engage at a first threshold and disengage at another threshold, which may control the time and pressures applied to the tissue site. The reduced-pressure source 132 may be turned on or off based on pressure applied, power utilized, or time elapsed.

The determination of the reduced pressure applied to the tissue site 102 may be performed utilizing any number of detection sensors or measurement elements. For example, one or more secondary conduits or lumens in the reduced-pressure delivery conduit 129 may measure the reduced pressure. Alternatively, the reduced pressure may be measured utilizing electronic sensors at the reduced-pressure connector 122. The electronic sensors that may measure conditions at the reduced-pressure connector 122 may communicate with the reduced-pressure source 132 utilizing a wired or a wireless connection. The cycles shown in FIG. 6 may be repeated a number of times.

In other embodiments, the pressure applied at the respective points may vary based on the treatment utilized for a particular patient. For example, between point B and C, the reduced pressure may decrease all the way to zero and remain there for a specified time period before reactivating the reduced-pressure source 132. Alternatively, the reduced pressure applied between point C and D may be increased more slowly than was initially applied and to a greater reduced pressure value.

Figure 7:
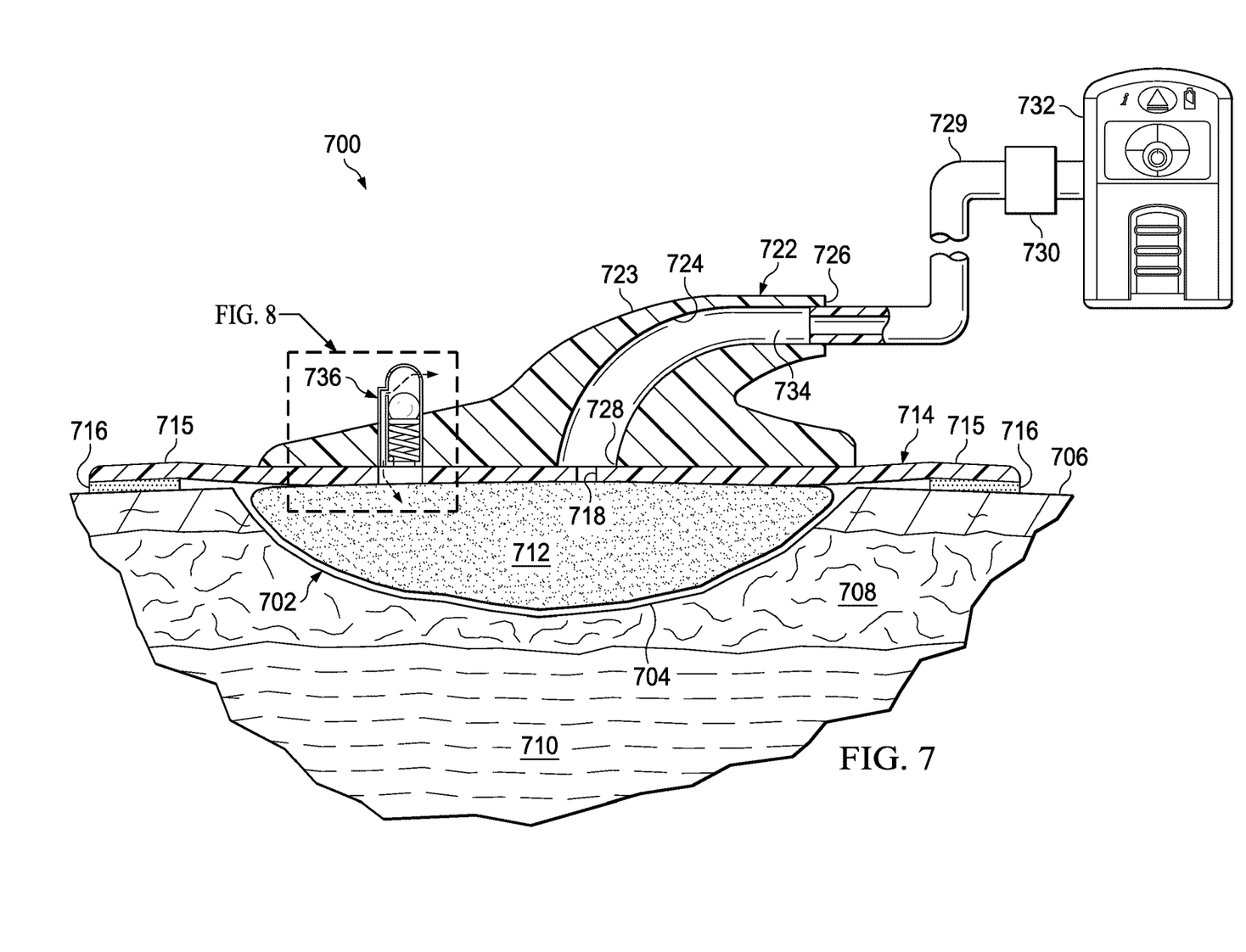
FIG. 7 is a schematic diagram with a portion shown in cross section of a reduced-pressure treatment system in accordance with an illustrative embodiment.
Figure 8:
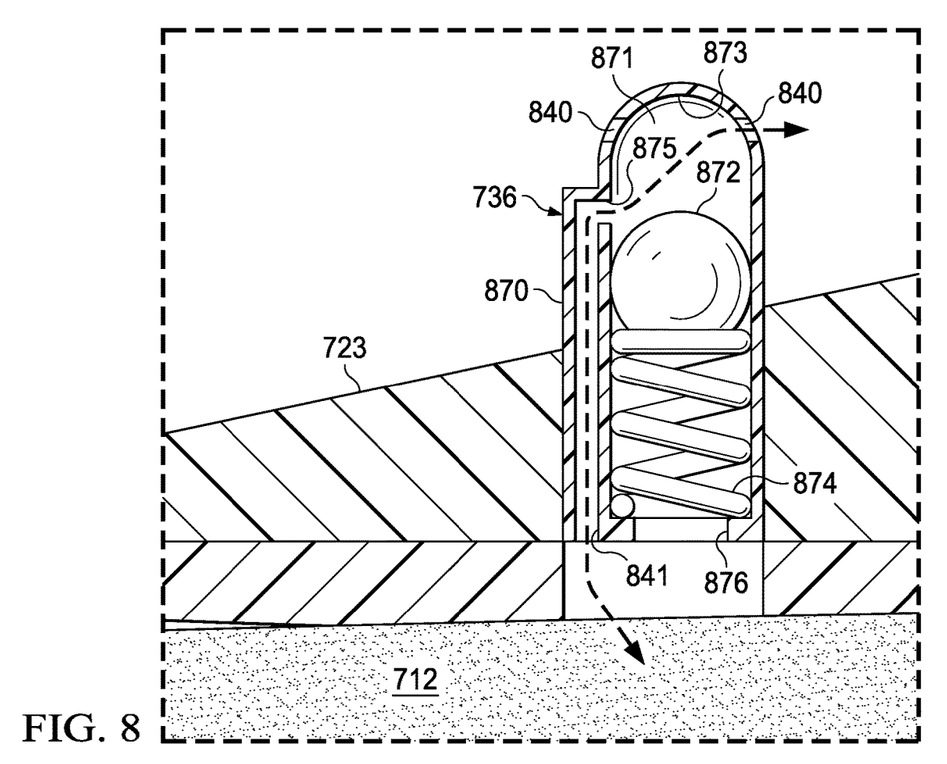
FIG. 8 is a cross-sectional view of a dressing valve in accordance with an illustrative embodiment.

Referring now primarily to FIGS. 7 and 8 another illustrative embodiment of a reduced-pressure connector 722 in a reduced-pressure treatment system 700 is presented. The reduced-pressure connector 722 of FIGS. 7 and 8 is an alternative embodiment. The reduced-pressure connector 722 includes a dressing valve 736 that is operable to vent air from the environment to a tissue site 702 in response to reaching a maximum, or elevated, reduced pressure. The dressing valve 736 includes a valve body 870 having a chamber 871, at least one venting aperture 840, a venting port 841, and a biasing member, such as spring 874. The dressing valve 736 allows a working gas to flow through the dressing valve 736 into the tissue site 702 in response to a specified reduced pressure being applied to the dressing valve 736.

The ball 872 may be formed from a plastic, metal, or a composite material. The ball 872 is configured to move slidably or roll up and down against the walls of the valve body 870 in the chamber 871. In particular, the ball 872 may provide an airtight seal between the ball 872 and a seat 873 of the valve body 870. The ball experiences reduced pressure delivered through an access aperture 876 regardless of the position of the ball 872 within the dressing valve 736. The ball 872 may alternatively be any number of sealing elements, such as a piston.

The spring 874 biases the ball 872 towards the seat 873. When the ball 872 is against the seat 873, an opening 875 of the venting port 841 into the chamber 871 is sealed and the at least one venting aperture 840 is sealed. The spring 874 is configured such that the ball 872 overcomes the biasing of the spring 874 when exposed to a reduced pressure greater than the maximum reduced pressure. Whereupon, a working gas enters the at least one venting aperture 840 and is communicated to the venting port 841.

The dressing valve 736 may include one or more venting apertures 840. At a regular or operating pressure, (e.g., −115 mm Hg) the ball 872 is at the top (for the orientation shown) of the dressing valve 736 in the seat 873 thereby sealing the venting apertures 840 from communicating air from the environment through the dressing valve 736. The spring 874 is a biased member that supports the ball 872. The spring 874 may alternatively be an elastomer, pneumatic or hydraulic element, or other biased element that maintains the ball 872 at the top of the dressing valve 736 at pressures below a threshold pressure.

The maximum pressure may represent a relief, or cracking value. The reduced pressure applied to the tissue site 702 is similarly applied to the dressing valve 736 and particularly to the ball 872 through the aperture 876. The aperture 876 ensures that the reduced pressures experienced underneath the reduced-pressure connector 722 and sealing member 714 are similarly applied within the dressing valve 736. For example, once the maximum pressure is reached, the ball 872 compresses the spring 874 sufficiently to allow air to be communicated through the venting apertures 840 to the venting port 841 for communication to the tissue site 702. As a result air or air bubbles may be introduced into the supply conduit thereby reducing any vacuum locks and furthering assisting with the removal of fluids or exudates from the tissue site 702. The dressing valve 736 may require a specified reduced pressure, or maximum reduced pressure to be applied against the ball 872 in order to compress the spring 874. The aperture 876 and venting port 841 may be sized differently to ensure that the pressure against the ball 872 is able to compress the spring 874. For example, the aperture 876 may be multiple times the diameter of the venting port 841, such that greater pressure may be applied to the ball 872 to reach the relief pressure. The venting port 841 may be configured or positioned to enable vented air to be channeled to a supply aperture 718.

As previously described, the venting apertures 840 may include filters for filtering air from the environment in which the reduced-pressure treatment system 700 is utilized. The dressing valve 736 may utilize filters or membranes to maintain sterility and prevent fluids from entering the dressing valve 736 through the aperture 876 or venting port 841. The dressing valve 736 may similarly be disengaged or deactivated utilizing a cover, switch or other elements. For example, the venting apertures 840 may be plugged or covered with a removable drape.

The illustrative embodiments may be utilized singly or in combination to reduce or prevent vacuum lock when extracting fluids from the tissue site 102. For example, elements of FIGS. 1-5, 7, and 8 may be combined. In a first embodiment, the reduced-pressure treatment system 100 may apply a reduced pressure to a wound site utilizing a reduced-pressure source to extract fluid from the tissue site 102. At a specified threshold or based on the configuration of the dressing valve 136 incorporated with the reduced-pressure treatment system 100, the dressing valve 136 is sealed, and allows the reduced pressure to increase.

Next, the reduced-pressure treatment system 100 determines whether the desired pressure is reached or a time period has expired. If the desired pressure is not reached, the reduced-pressure source 132 continues to increment the reduced pressure applied to the reduced-pressure connector 122 and corresponding tissue site 102. If the desired pressure is reached, or a time period expires, the reduced-pressure source 132 is deactivated. The determination of the desired pressure may be determined by the reduced-pressure source 132 using the suction or power applied, sensors, sensing lumens within the reduced-pressure delivery conduit or any number of other detection elements or sensors. The reduced-pressure source 132 ensures that the reduced pressure applied to the tissue site 102 remains as stable as possible once the reduced-pressure source 132 is deactivated.

The reduced-pressure treatment system 100 may begin to lose pressure due to natural leaks. For example, air may seep through edges of the sealing member 114 to enter the tissue site 102. Alternatively, the materials of the reduced-pressure connector 122 and the sealing member 114 may be semi-permeable to air allowing small amounts of air to naturally decrease the pressure applied to the tissue site 102. In yet another embodiment, one or more of the venting apertures 140 of the dressing valve 136 may communicate directly with the supply aperture 118 allowing a small amount of ambient air or a working gas to slowly break up a potential static column of fluid. The air or working gas that is communicated through the dressing valve 136 may be controlled and filtered to prevent desiccation of the tissue site 102. Air introduced through the dressing valve 136 may be filtered to ensure that contaminants are not introduced to the tissue site 102 thereby causing infection or other problems that may affect healing of the tissue site 102.

At a specified threshold, the dressing valve 136 becomes unsealed and introduces additional air to the tissue site 102. The air introduced through release of the dressing valve 136 or through natural leakage may break up a static column of fluid causing a vacuum lock or otherwise allow the fluids to be extracted through the reduced-pressure delivery conduit 129 to the reduced-pressure source 132 or a corresponding fluid housing, canister, or reservoir. The specified threshold at which the dressing valve 136 becomes unsealed may correspond to the materials utilized for forming the dressing valve 136. For example, in the case of the flexible member 138, the thickness of the flexible member 138 may govern when the dressing valve 136 both collapses to seal the venting port 141 and unseals the venting port 141 to vent air to the tissue site 102.

In response to reaching a desired minimum threshold pressure or expiration of a time period, the reduced-pressure treatment system 100 may once again apply a reduced pressure to the tissue site 102 utilizing the reduced-pressure source 132. For example, the reduced-pressure source 132 may be reactivated based on sensed conditions. The reduced-pressure source 132 may simply utilize a timer for turning on and off the reduced-pressure source 132.

The reduced-pressure treatment system 700 may apply a reduced pressure to a tissue site 702 utilizing a reduced-pressure source 732 to extract fluid from a tissue site 702. At pressures utilized for treatment, the dressing valve 736 is sealed allowing the reduced pressure to be maintained at the tissue site 702. In response to a timer or other indication, the reduced pressure may be increased. For example, every 10 minutes the reduced pressure applied to the tissue site 702 may be increased by 50 mm Hg to reach a maximum reduced pressure at which point the dressing valve 736 may release air through the venting port 841 to the tissue site 702 for extraction through the body conduit 724. The maximum reduced pressure may be, for example and without limitation, −115, −120, −130, −140, −150, −160, −170, −180, −190, −120 mm Hg or another pressure. As a result, any fluids within the reduced-pressure delivery conduit 729 and tissue site 702 may be broken up by the introduction of air or working gas thereby allowing the fluids to be more easily removed.

At the maximum threshold or relief pressure, the dressing valve 736 opens introducing the working gas. The introduction of working gas may cause the spring 874 to reseat the ball 872. At that point, the reduced-pressure treatment system 700 returns to a desired reduced pressure that corresponds to a standard treatment pressure. The reduced pressure may be periodically incremented to open the dressing valve 736 and thereby overcome static fluid buildup or vacuum lock that may occur.

The reduced-pressure source 732 may include components that determine whether a minimum threshold pressure has been reached. The determination may be performed utilizing one or more lumens of a reduced-pressure delivery conduit between the reduced-pressure source 732 and the dressing valve 736. For example, a primary lumen of the supply conduit may extract fluid from the tissue site 702, and a secondary lumen may measure the reduced pressure applied to the tissue site 702 by the reduced-pressure source 732. The reduced-pressure source 732 continues to apply a reduced pressure to the tissue site 702.

Figure 9:
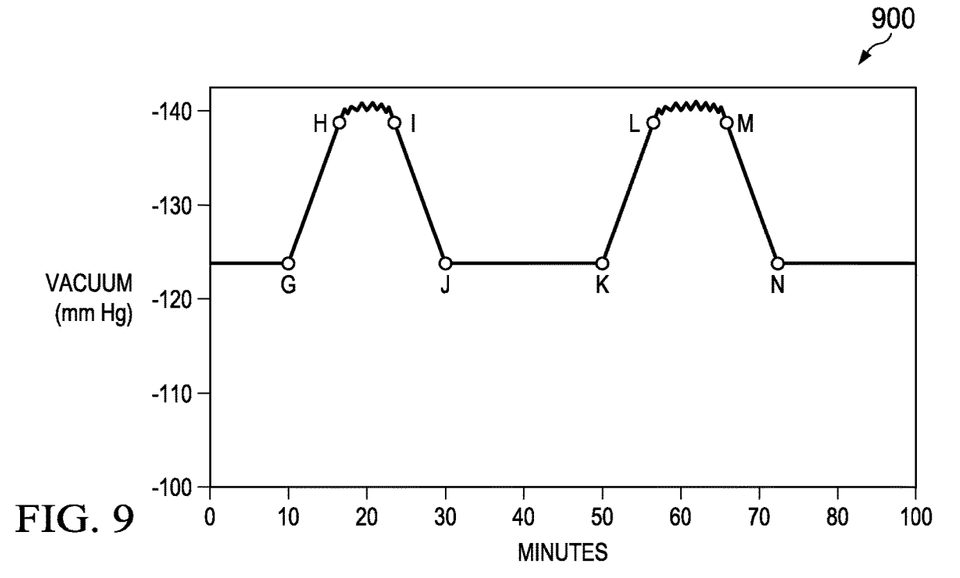
FIG. 9 is a graph illustrating pressure applied by the reduced-pressure connector over time in accordance with an illustrative embodiment.

Referring now to FIGS. 7, 8, and 9, and primarily to FIG. 9, a chart 900 presents pressure and time graph from use of the reduced-pressure treatment system 700. The nature of the chart 900 is analogous to chart 600 in FIG. 6. The reduced-pressure treatment system 700 may utilize the dressing valve 736 for releasing a working gas through the reduced-pressure connector 722. In chart 900, the reduced pressure applied may begin at a level as shown (i.e. −125 mm Hg). At point G, the reduced-pressure source may begin to increase the reduced pressure until it reaches point H, which is the maximum reduced pressure.

At point H, the dressing valve 736 may release air through the venting port 841 to the reduced-pressure connector 722 to break up or alleviate a vacuum lock. Point H represents a maximum or cracking or relief pressure that engages the dressing valve 736 to release air for reducing vacuum lock. Between points H and I, the dressing valve 736 may allow air to be released through the venting port 841.

At point I to J the reduced-pressure source 732 naturally or mechanically reduces the reduced pressure until the original pressure is reached at point J. Between points J and K, the reduced pressure continues to be applied to the tissue site 702. The time between the points in chart 900 may be controlled by timing mechanisms within the reduced-pressure source 732. Alternatively, logic, circuitry, processors, or sensors within the reduced-pressure source 732 may increase or decrease the reduced pressure to reach the relief pressure shown between points H and I and L and M.

For example, the user may utilize an interface or mechanical controls to configure the pressures and time between each point based on the desired level and method of treatment. The relief pressure that allows the body conduit to be released or partially vented between points H and I and L and M may ameliorate a vacuum lock. Similarly, the opening of the dressing valve in chart 600 between points B and C and E and F may provide similar functionality.

The present invention and its advantages have been disclosed in the context of certain illustrative, non-limiting embodiments. The illustrative descriptions above are not intended to be exhaustive or to limit the invention to the precise forms disclosed. Moreover, it should be understood that various changes, substitutions, permutations, and alterations can be made without departing from the scope of the invention as defined by the appended claims. It will be appreciated that any feature that is described in a connection to any one embodiment may also be applicable to any other embodiment. For example, without limitation, the general statements related to the embodiments of FIGS. 1-6 may apply to the embodiment of FIG. 7-8.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

Where apparent from context, certain features of the devices or systems are described "in use."

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A method for alleviating a vacuum lock during a reduced-pressure treatment of a tissue site, the method comprising:
    applying a reduced pressure to the tissue site utilizing a treatment system;
    sealing a dressing valve of the treatment system at a first threshold pressure; and
    if the reduced pressure decreases, unsealing the dressing valve to release a working gas into one or more venting apertures of the dressing valve for extraction by a body conduit of the treatment system to alleviate vacuum lock, wherein the reduced pressure decrease corresponds to an increase in absolute pressure underneath the dressing.

2. The method of claim 1, wherein the treatment system includes a sealing member and a reduced-pressure connector positioned over the tissue site in fluid communication with a reduced-pressure source through a reduced-pressure delivery conduit.

3. The method of claim 1, wherein the working gas is air.

4. The method of claim 1, wherein sealing the dressing valve of the treatment system comprises collapsing a flexible member against a port aperture to seal the port aperture.

5. The method of claim 1, wherein sealing the dressing valve of the treatment system comprises collapsing at least a portion of a flexible member into a venting port.

6. The method of claim 1, wherein sealing the dressing valve of the treatment system comprises blocking venting apertures of a flexible member by collapsing a portion of the flexible member into a venting port to prevent fluid communication between a port aperture and the venting apertures.

7. A method for alleviating a vacuum lock during reduced-pressure treatment of a tissue site, the method comprising:
applying a reduced pressure to the tissue site utilizing a treatment system;
increasing the reduced pressure applied to the tissue site by the treatment system;
determining the reduced pressure applied to the tissue site by the treatment system;
venting a working gas through a dressing valve of the treatment system to a reduced-pressure delivery conduit in fluid communication with a reduced-pressure source to alleviate vacuum locks in response to determining that the reduced pressure has reached a relief pressure; and
resealing the dressing valve.

8. The method of claim 7, wherein the treatment system includes a sealing member and a reduced-pressure connector positioned over the tissue site and in fluid communication with the reduced-pressure source through the reduced-pressure delivery conduit.

9. The method of claim 7, wherein venting releases the working gas for extraction through the reduced-pressure delivery conduit to reduce effects of vacuum lock.

* * * * *